(12) United States Patent
Uchida et al.

(10) Patent No.: US 8,993,791 B2
(45) Date of Patent: Mar. 31, 2015

(54) PROCESS FOR PRODUCING EPOXY COMPOUNDS

(75) Inventors: Hiroshi Uchida, Minato-ku (JP);
Takamitsu Kobayashi, Minato-ku (JP);
Naoya Fukumoto, Minato-ku (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 13/515,707

(22) PCT Filed: Dec. 17, 2010

(86) PCT No.: PCT/JP2010/072801
§ 371 (c)(1),
(2), (4) Date: Jun. 13, 2012

(87) PCT Pub. No.: WO2011/078091
PCT Pub. Date: Jun. 30, 2011

(65) Prior Publication Data
US 2012/0302775 A1    Nov. 29, 2012

(30) Foreign Application Priority Data

Dec. 24, 2009 (JP) .................................. 2009-292188

(51) Int. Cl.
*C07D 301/03* (2006.01)
*C07D 301/12* (2006.01)
*C07D 303/28* (2006.01)

(52) U.S. Cl.
CPC ............ *C07D 301/12* (2013.01); *C07D 303/28* (2013.01)
USPC ........................................................ 549/523

(58) Field of Classification Search
USPC ........................................................ 549/523
See application file for complete search history.

(56) References Cited

U.S. PATENT DOCUMENTS

| 3,053,856 | A | 9/1962 | Payne et al. |
| 5,608,088 | A | 3/1997 | Watanabe et al. |
| 6,326,508 | B1 | 12/2001 | Godbole et al. |
| 2004/0068127 | A1 | 4/2004 | Schoebrechts et al. |

FOREIGN PATENT DOCUMENTS

| CN | 1438222 | A |   | 8/2003 |
| JP | 59-227872 | A |   | 12/1984 |
| JP | 62-114979 | A |   | 5/1987 |
| JP | 7-206835 | A |   | 8/1995 |
| JP | 08-081402 | A |   | 3/1996 |
| JP | 10-212281 | A |   | 8/1998 |
| JP | 2004-508285 | A |   | 3/2004 |
| JP | 2004-099445 | A |   | 4/2004 |
| JP | 2004-238331 | A |   | 8/2004 |
| JP | 2006-028057 | A |   | 2/2006 |
| JP | 2006-160609 | A |   | 6/2006 |
| JP | 2008239579 |   | * | 9/2008 |
| JP | 2008-239579 | A |   | 10/2008 |
| JP | 2009-102388 | A |   | 5/2009 |

OTHER PUBLICATIONS

George B. Payne et al., "Reactions of Hydrogen Peroxide. VII. Alkali-Catalyzed Epoxidation and Oxidation Using a Nitride as Co-reactant", The Journal of Organic Chemistry, 1961, pp. 659-663, vol. 26, No. 3.

R. D. Bach et al., "Epoxidation of Olefins by Hydrogen Peroxide-Acetonite, cis-Cyclooctene Oxide", Organic Syntheses, 1981, pp. 63-66, vol. 60.

International Search Report of PCT/JP2010/072801 dated Jan. 25, 2011.

Extended European Search Report for Application No. 10839321.6 dated Mar. 4, 2014; 6 pages.

* cited by examiner

*Primary Examiner* — T. Victor Oh
(74) *Attorney, Agent, or Firm* — Sughrue Mion, PLLC

(57) ABSTRACT

To provide an efficient method of producing an epoxy compound comprising reacting hydrogen peroxide and acetonitrile with the carbon-carbon double bond of an organic compound having a carbon-carbon double bond. A method of producing an epoxy compound comprising epoxidizing the carbon-carbon double bond of an organic compound having a carbon-carbon double bond in the presence of acetonitrile by using hydrogen peroxide as an oxidizing agent, wherein the reaction proceeds while controlling the acetonitrile concentration in the reaction system in the range of 0.6-5 mol/L by using a solvent containing an alcohol.

12 Claims, No Drawings

PROCESS FOR PRODUCING EPOXY COMPOUNDS

CROSS REFERENCE TO RELATED APPLICATIONS

This application is a National Stage of International Application No. PCT/JP2010/072801 filed Dec. 17, 2010, the contents of which are incorporated herein by reference in their entirety.

TECHNICAL FIELD

The present invention relates to a method of producing epoxy compounds. More specifically, the present invention relates to a method of producing an epoxy compound, wherein the carbon-carbon double bond of an organic compound having a carbon-carbon double bond can be epoxidized with high efficiency in the presence of acetonitrile by using hydrogen peroxide as an oxidizing agent.

BACKGROUND ART

Epoxy compounds are used in a variety of applications utilizing the ring-opening of an oxirane ring of 1,2-epoxide. In particular, bisphenol A type epoxy resins and novolak type epoxy resins are widely used as materials for semiconductor encapsulants, due to the ease of mass production and low cost, and excellent resistance to heat and water.

Conventionally known epoxy compounds are mainly produced by reacting a compound having a phenolic hydroxyl group with epihalohydrin, and epoxy compounds thus produced contain an organic halogen. Therefore, it is difficult for them to be used as an encapsulant for recent highly integrated semiconductors in terms of reliability. Under such circumstances, considerable efforts have been made to develop methods of producing halogen-free epoxy compounds that do not use epihalohydrin as a raw material, and as such a method, a method of oxidizing the carbon-carbon double bond of an olefin with an oxidizing agent is known.

As the oxidizing agent, a peracid, such as peracetic acid and perbenzoic acid, has been used. However, in such a method, an equivalent amount of acid derived from the oxidizing agent is produced, and thus corrosion, etc., of equipment may occur. In contrast, hydrogen peroxide is inexpensive and non-corrosive, and do not generate byproducts or only water is generated after the reaction. Therefore, hydrogen peroxide is environmentally-friendly and excellent as an oxidizing agent for industrial use.

As one of the methods of producing an epoxy compound from an olefin by using hydrogen peroxide as the oxidizing agent, a method of reacting hydrogen peroxide and an organic nitrile compound with a carbon-carbon double bond in the presence of a basic salt compound, such as a carbonate and a bicarbonate of an alkali metal (see Patent Documents 1-3, and Non-Patent Document 1 below).

Patent Document 1 discloses a method of producing an epoxy compound comprising reacting a polyallylether compound with hydrogen peroxide in the presence of acetonitrile while controlling the pH of the reaction system at 7.5 or higher. However, Patent Document 1 describes controlling the pH of the reaction system and replenishing hydrogen peroxide during the progress of the reaction, but does not describe controlling the concentration of acetonitrile.

Patent Document 2 discloses a method of producing a tricyclopentadiene diepoxide comprising reacting tricyclopentadiene and hydrogen peroxide in the presence of a nitrile compound in an aqueous inorganic acid salt solution. However, Patent Document 2 describes that the pH of the reaction system affects the yield and selectivity of tricyclopentadiene diepoxide, but does not describe controlling the concentrations of hydrogen peroxide and acetonitrile in the reaction system.

Patent Document 3 discloses a method of producing an epoxy compound having an adamantane backbone comprising reacting an allyloxy compound having an adamantane backbone, a nitrile compound and hydrogen peroxide water in the presence of a basic compound. However, Patent Document 3 describes adjusting the pH of the reaction mixture, but does not describe controlling the concentrations of hydrogen peroxide and acetonitrile in the reaction system.

Non-Patent Document 1 discloses a method of producing a cis-cyclooctene oxide comprising reacting cis-cyclooctene, a nitrile compound and hydrogen peroxide water in the presence of potassium carbonate. However, non-Patent Document 1 does not describe in detail controlling the concentration of each component in the reaction system during the progress of the reaction.

Even though the initial charging amount of each component at the beginning of the reaction is described in the above prior art documents, none of the above prior art documents describe controlling the concentration of acetonitrile in the reaction system during the progress of the reaction.

PRIOR ART DOCUMENTS

Patent Documents

Patent Document 1: Japanese Unexamined Patent Publication (Kokai) No. 59-227872
Patent Document 2: Japanese Unexamined Patent Publication (Kokai) No. 2004-99445
Patent Document 3: Japanese Unexamined Patent Publication (Kokai) No. 2008-239579

Non-Patent Documents

Non-Patent Document 1: Organic Synthesis, Vol. 60, pp. 63-66 (1981)

SUMMARY OF THE INVENTION

Problems to be Solved by the Invention

The object of the present invention is to provide an efficient method of producing an epoxy compound, wherein hydrogen peroxide and acetonitrile are reacted with the carbon-carbon double bond of an organic compound having a carbon-carbon double bond.

Means to Solve the Problems

As the result of intensive and extensive study to solve the above problems, the present inventors have found that by allowing the reaction to proceed while controlling the acetonitrile concentration in the reaction system in a predetermined concentration range by using an alcohol-containing solvent, in a method of producing an epoxy compound comprising epoxidizing the carbon-carbon double bond of an organic compound having a carbon-carbon double bond in the presence of acetonitrile by using hydrogen peroxide as an oxidizing agent, an epoxy compound can be produced with high efficiency, and thereby have achieved the present invention.

More specifically, the present invention includes embodiments described below.

[1] A method of producing an epoxy compound comprising epoxidizing the carbon-carbon double bond of an organic compound having a carbon-carbon double bond in the presence of acetonitrile by using hydrogen peroxide as an oxidizing agent, wherein the reaction proceeds while controlling the acetonitrile concentration in the reaction system in the range of 0.6-5 mol/L by using a solvent containing an alcohol.

[2] The method of producing an epoxy compound according to the above [1], wherein the ratio of the total amount used of acetonitrile to the total amount used of hydrogen peroxide (acetonitrile/hydrogen peroxide (molar ratio)) in the reaction is in the range of 0.6-2.

[3] The method of producing an epoxy compound according to the above [1] or [2], wherein the ratio of the total amount used of acetonitrile to the total amount used of the organic compound having a carbon-carbon double bond (acetonitrile/the carbon-carbon double bond of the organic compound having a carbon-carbon double bond (molar ratio)) in the reaction is in the range of 1.2-5.

[4] The method of producing an epoxy compound according to any one of the above [1] to [3], wherein the pH of the reaction mixture during the progress of the reaction is in the range of 9-11.

[5] The method of producing an epoxy compound according to any one of the above [1] to [4], wherein the alcohol is at least one selected from C1-C4 alcohols.

[6] The method of producing an epoxy compound according to any one of the above [1] to [5], wherein the temperature of the reaction mixture is controlled in the range of 20-100° C.

[7] The method of producing an epoxy compound according to any one of the above [1] to [6], wherein acetonitrile is added to a concentration of 5 mol/L or less before the acetonitrile concentration in the reaction system reaches less than 0.6 mol/L as the reaction proceeds.

[8] The method of producing an epoxy compound according to any one of the above [1] to [7], wherein the organic compound having a carbon-carbon double bond is an organic compound having two or more allylether groups.

[9] The method of producing an epoxy compound according to the above [8], wherein the organic compound having two or more allylether groups is at least one selected from the group consisting of bisphenol A type diallylether, bisphenol F type diallylether, tetramethylbiphenol diallylether, and an aliphatic polyallylether.

[10] The method of producing an epoxy compound according to the above [1], wherein the organic compound having a carbon-carbon double bond is bisphenol A type diallylether and/or bisphenol F type diallylether, and the acetonitrile concentration in the reaction system is in the range of 0.6-2 mol/L.

[11] The method of producing an epoxy compound according to any one of the above [1] to [10], wherein the acetonitrile is a crude acetonitrile obtained as a byproduct of acrylonitrile production by the Sohio process.

Effects of the Invention

According to the method of producing an epoxy compound of the present invention, an epoxy compound can be safely produced by reacting an organic compound having a carbon-carbon double bond and hydrogen peroxide in a simple procedure with high efficiency and low cost. Thus, the present invention makes substantial contributions to the industry.

MODE FOR CARRYING OUT THE INVENTION

The present invention will now be explained in detail below.

The method of producing an epoxy compound according to the present invention is characterized in that in a method of producing an epoxy compound comprising epoxidizing the carbon-carbon double bond of an organic compound having a carbon-carbon double bond (hereinafter referred to as "substrate") in the presence of acetonitrile by using hydrogen peroxide as an oxidizing agent, the reaction proceeds while controlling the acetonitrile concentration in the reaction system in the range of 0.6-5 mol/L by using a solvent containing an alcohol.

In the present invention, hydrogen peroxide is used as the oxidizing agent, and as a source for the hydrogen peroxide, it is preferable that an aqueous solution of hydrogen peroxide be used. The concentration of hydrogen peroxide may typically be selected from, but not limited to, the range of 1-80% by weight, preferably 10-60% by weight. From the viewpoint of industrial productivity and energy cost during separation, high concentration of hydrogen peroxide may be preferred, whereas from the viewpoint of economy and safety, it is preferable that using an excessively high concentration of and/or an excess amount of hydrogen peroxide be avoided.

The amount used of hydrogen peroxide may not be specifically limited. The hydrogen peroxide concentration in the reaction system decreases as the reaction proceeds. It is preferable that, by replenishing hydrogen peroxide in order to compensate this decrease, the hydrogen peroxide concentration in the reaction system be maintained in the range of 1-30% by weight, more preferably 2-10% by weight. If the concentration is less than 1% by weight, productivity may be adversely affected, whereas if it exceeds 30% by weight, hydrogen peroxide in a mixed composition of alcohol and water tends to be more explosive and thus may be dangerous. If a large amount of hydrogen peroxide is charged into the reaction system at the initial stage of the reaction, the reaction may rapidly proceed and may be dangerous, and thus it is preferable that hydrogen peroxide be added slowly into the reaction system as described below.

The concentration of acetonitrile in the reaction system for use in the method of producing an epoxy compound according to the present invention may be controlled to be in the range of 0.6-5 mol/L during the progress of the reaction. In a method of producing an epoxy compound comprising epoxidizing the carbon-carbon double bond of an organic compound having a carbon-carbon double bond in the presence of acetonitrile by using hydrogen peroxide as an oxidizing agent, it is believed that acetonitrile and hydrogen peroxide may react to produce an oxidized active species (perimidic acid), and this oxidized active species may oxidize the carbon-carbon double bond. Therefore, the theoretical amount required of acetonitrile in this reaction may be equivalent (equal moles) to the amount of the carbon-carbon double bond of the organic compound, and the concentration of acetonitrile in the reaction system decreases as the reaction proceeds. If the concentration in the reaction system is less than 0.6 mol/L, the yield may decrease, while if it exceeds 5 mol/L, the epoxidation selectivity of hydrogen peroxide may tend to decrease, leading to higher cost, which may be undesirable. Thus, it is preferable that the concentration of acetonitrile be controlled by setting the initial concentration at the beginning of the reaction in the above concentration range, monitoring the concentration during the progress of the reaction, and replenishing acetonitrile within the range not exceeding the upper limit before the concentration reaches below the lower limit value described above. It is preferable that the concentration be 0.7 mol/L or greater and 2 mol/L or less.

In addition, in the method of producing an epoxy compound according to the present invention, alcohol coexists in the reaction system. The alcohol may serve as a solvent for the substrate (an organic compound having a carbon-carbon double bond) and as a viscosity-lowering agent for enhancing the transfer rate of hydrogen peroxide to the substrate when the viscosity of the substrate is high. When an aqueous solution of hydrogen peroxide is used as the source for hydrogen peroxide and the hydrophilicity of the substrate (an organic compound having a carbon-carbon double bond) is low, the alcohol may turn an organic layer containing the substrate and acetonitrile and an aqueous layer containing hydrogen peroxide into a homogeneous system, thereby enhancing the reaction rate. In this case, if alcohol is not present or the amount used is insufficient, separation into two layers may occur in the reaction system, and as a result, the epoxidation selectivity of hydrogen peroxide decreases. It is preferable that the alcohol be a C1-C4 alcohol, more preferably a C1-C4 primary alcohol, and still more preferably methanol, ethanol and 1-propanol. Bisphenol A type diallylether and/or bisphenol F type diallylether used as an organic compound having a carbon-carbon double bond may be soluble in alcohol or acetonitrile. However, if the amount used of acetonitrile is excessive, cost may increase. In contrast, in the method of producing an epoxy compound according to the present invention, by relatively increasing the amount used of an inexpensive alcohol, the amount used of acetonitrile in the reaction system may be reduced. In addition, by controlling the acetonitrile concentration in the reaction system in the range of 0.6-5 mol/L, the substrate may be converted at a high conversion rate. It is preferable that the ratio of the total amount of acetonitrile to the total amount of hydrogen peroxide used in the reaction be 0.6-2, and more preferably 0.65-1.85 (molar ratio).

It is preferable that the charging amount of acetonitrile at the beginning of the reaction be in the range of 1.2-5 molar equivalents, and more preferably 1.5-3 molar equivalents, based on the number of the double bond of an organic compound having a carbon-carbon double bond. If it is less than 1.2 molar equivalent, the yield may decrease, while if it is greater than 5 molar equivalents, the epoxidation selectivity of hydrogen peroxide may tend to decrease, leading to higher cost, which may be undesirable. The charging amount of acetonitrile at the beginning of the reaction should satisfy the above concentration range of 0.6-5 mol/L in the reaction system during the progress of the reaction. When acetonitrile is replenished during the reaction, it is preferable that the ratio of the total amount used of acetonitrile to the total amount used of the organic compound having a carbon-carbon double bond (acetonitrile/the carbon-carbon double bond of the organic compound having a carbon-carbon double bond (molar ratio)) for use in the reaction also satisfy the above range, i.e., 1.2-5, more preferably 1.5-3. The source of acetonitrile for use in the present invention is not specifically limited, and a crude acetonitrile obtained, for example, as a byproduct during the production of acrylonitrile by the Sohio process may be used, as well as a commercial product. Using a crude acetonitrile may reduce the production cost.

The Sohio process (vapor phase catalytic ammooxidation reaction) is a vapor phase catalytic oxidation reaction for producing acrylonitrile by reacting propylene or propane with ammonia and oxygen in the presence of a catalyst, followed by separation and purification of the reaction gas. When propylene is used, it may be expressed in the following equation:

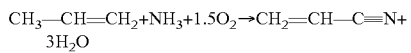

$$CH_3-CH=CH_2+NH_3+1.5O_2 \rightarrow CH_2=CH-C\equiv N + 3H_2O$$

In the above reaction, a crude acetonitrile is obtained as a byproduct together with hydrogen cyanide (HCN), water and other impurities (see, for example, Japanese Unexamined Patent Publication (Kokai) No. 2004-10579, and Japanese Unexamined Patent Publication (Kokai) No. 2009-102388). The crude acetonitrile obtained as a byproduct contains various impurities, and the relative ratio of the components may widely vary depending on a variety of conditions. In general, the composition of a crude acetonitrile obtained from an acrylonitrile plant may be, but not limited to, 10%-30% by weight of water and 25%-85% by weight of acetonitrile. A crude acetonitrile may typically contain about 81% by weight of acetonitrile, about 17% by weight of water, about 0.5% by weight of hydrogen cyanide, about 0.1% by weight of acrylonitrile and about 1.4% by weight of other organic impurities.

In the method of producing an epoxy compound according to the present invention, it is preferable that the pH of the reaction mixture be in the range of 9-11, more preferably 9.5-11, and still more preferably 10-11. If the pH is lower than 9, the reaction rate may decrease, and thus productivity decreases. On the other hand, when it is higher than 11, the reaction may rapidly proceed, which may be dangerous, and may decrease yield, which may not be desirable. When a compound having two carbon-carbon double bonds is used as an organic compound having a carbon-carbon double bond, the yield and selectivity of diepoxide may be affected by the pH of the reaction system. It is preferable that the pH is in the range of 10-11, since both the yield and selectivity of diepoxide may be enhanced.

A basic salt compound for use in adjusting the pH in the reaction system includes an inorganic base salt, such as potassium carbonate, potassium bicarbonate, potassium hydroxide, sodium hydroxide and cesium hydroxide, and an organic base salt, such as potassium methoxide, potassium ethoxide, sodium methoxide, sodium ethoxide and tetramethyl ammonium hydroxide. Potassium carbonate, potassium bicarbonate, potassium hydroxide, sodium hydroxide, potassium methoxide, potassium ethoxide, sodium methoxide and sodium ethoxide may be preferred, since adjustment of the pH is easy. Potassium hydroxide and sodium hydroxide are highly soluble in water and alcohols and are highly reactive, and thus may be more preferred.

The basic salt compound may be used in an aqueous solution or an alcoholic solution. An alcohol that can be used as a solvent for the alcoholic solution includes methanol, ethanol, propanol and butanol, and it is preferable that the same alcohol as the above-mentioned reaction solvent be used. It is preferable that the solution of a basic salt compound be added so that the pH of the reaction mixture is not below 9 due to the addition of hydrogen peroxide. In this case, it is preferable that the addition be carried out so that the temperature of the reaction mixture is maintained in the range of 20-100° C., more preferably 25-60° C.

In the method of producing an epoxy compound according to the present invention, the reaction temperature may typically be in the range of 20-100° C., preferably 25-60° C. The reaction time may vary depending on the reaction temperature and is not particularly limited, but it may typically be in the range of 4-48 hours, preferably 4.5-32 hours.

The substrate subjected to epoxidation in the method of producing an epoxy compound according to the present invention is an organic compound having a carbon-carbon double bond without any limitation, but an organic compound having an allylether group may be preferred. The term "allylether group" as used herein refers to a "C=C—C—O—" bond, i.e., an allyloxy group. The number of carbon-carbon double bonds contained in the compound may be one, or two or more. A compound having one carbon-carbon double bond includes phenylallyl ether, cresol monoallyl ether, cyclooxene, and cyclooctene. A compound having two or more carbon-carbon double bonds includes 3,4-cyclohexenylmethyl-3',4'-cyclohexene carboxylate, an allylether compound of a novolak type phenolic resin, trimethylol propane triallylether, and pentaerythritol tetraallylether.

As described above, by controlling the pH of the reaction mixture in the range of 9-11, preferably 10-11, when an organic compound having a plurality of carbon-carbon double bonds, e.g., an organic compound having two or more allylether groups, is used, the corresponding polyepoxide can be obtained with high yield and selectivity. In particular, it is preferable that a compound having aromatic rings and two or more allylether groups represented by the following formula:

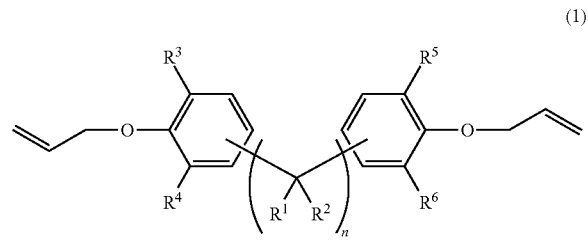

(1)

wherein, R¹ and R² independently represent a hydrogen atom, a C1-C6 alkyl group, a C2-C6 alkenyl group, a cycloalkyl group, such as a C3-C12 cycloalkyl group, or an aryl group, such as a C6-C10 aryl group, or R¹ and R² may together form a C2-C6 alkylidene group or a C3-C12 cycloalkylidene group;

R³, R⁴, R⁵ and R⁶ independently represent a hydrogen atom, a C1-C10 alkyl group, a C2-C10 alkenyl group, a cycloalkyl group, such as a C3-C12 cycloalkyl group, or an aryl group, such as a C6-C10 aryl group; and n represents an integer of 0 or 1, be used. When n is 0, two benzene rings are directly bound (forming a biphenyl backbone).

More specifically, such an organic compound includes a bisphenol A type diallylether, such as bisphenol A diallylether, 2,6,2',6'-tetramethylbisphenol A diallylether, 2,2'-diallylbisphenol A diallylether and 2,2'-di-t-butylbisphenol A diallylether, a bisphenol F type diallylether, such as bisphenol F diallylether, 2,6,2',6'-tetramethylbiphenol diallylether, 2,2'-diisopropylbiphenol diallylether, 4,4'-ethylidenebisphenol diallylether, 4,4'-cyclohexylidene bisphenol diallylether, 4,4'-(1-α-methylbenzylidene)bisphenol diallylether, 4,4'-(3,3,5-trimethylcyclohexylidene)bisphenol diallylether, and 4,4'-(1-methyl-benzylidene)bisphenol diallylether.

A biphenol type diallylether having aromatic rings and two allylether groups includes 2,2'-biphenyl diallylether, and tetramethylbiphenyl diallylether.

An aliphatic polyallylether having two allylether groups includes 1,5-pentanediol diallylether, 1,6-hexanediol diallylether, 1,9-nonanediol diallylether, 1,10-decanediol diallylether, and neopentylglycol diallylether.

An alicyclic polyallylether having two allylether groups includes 1,4-cyclohexanedimethanol diallylether, and tricyclo[5.2.1.0²·⁶]decanedimethanol diallylether.

It is preferable that an organic compound having two or more allylether groups be selected from the group consisting of a bisphenol A type diallylether, a bisphenol F type diallylether, a tetramethylbiphenol diallylether, and an aliphatic polyallylether.

In the method of producing an epoxy compound according to the present invention, the concentration of an organic compound having a carbon-carbon double bond may typically be adjusted to be in the range of 0.2-2 mol/L, preferably 0.3-1.5 mol/L. If the substrate concentration in the reaction system is less than 0.2 mol/L, productivity may decrease. On the other hand, if it exceeds 2 mol/L, the yield may decrease, which is unfavorable.

In view of stable industrial production, it is preferable that an epoxidation method comprises first charging acetonitrile and a substrate into a reactor, and then slowly adding hydrogen peroxide, while maintaining the reaction temperature as constant as possible and monitoring the consumption of hydrogen peroxide by the reaction. In such a method, the amount accumulated of hydrogen peroxide may be small and thus pressure rise can be minimized, even if oxygen gas is generated by the abnormal decomposition of hydrogen peroxide in the reactor. Since hydrogen peroxide vigorously decomposes in a high alkaline environment, it is preferable that the pH be adjusted at about 9-10 at the initial stage of the reaction, and then together with the addition of hydrogen peroxide, the pH of the reaction mixture be gradually controlled to about 10-11 as needed.

After the completion of the reaction, the reaction mixture may be diluted with pure water, or may be neutralized by adding thereto an acid, such as sulfuric acid, as needed, followed by dilution with pure water, the solvent may be evaporated and the residue may be extracted with an organic solvent, such as ethyl acetate.

After concentrating the organic layer thus separated from the aqueous layer, the resulting epoxy compound can be collected by a conventional method, such as distillation, chromatographic separation, recrystallization and sublimation.

EXAMPLES

The present invention is concretely explained by means of the Examples, which should not be construed to limit the present invention in any way.

Example 1

Into a 50 mL separable flask of a reaction calorimeter (MultiMax, manufactured by Mettler Toledo), bisphenol A type diallylether (5.00 g, 16.2 mmol, manufactured by Qin yang Tianyi Chemical Co., Ltd.), acetonitrile (2.67 g, 65.0 mmol, manufactured by Junsei Chemical Co., Ltd.) and ethanol (26.41 g, 573.4 mmol, manufactured by Junsei Chemical Co., Ltd.) were charged. At this stage, the acetonitrile concentration in the system was 1.56 mmol/L and the pH was 7.4. Then, a potassium hydroxide (manufactured by Wako Pure Chemical Industries, Ltd.)/ethanol solution (KOH/EtOH=250 mg/mL) was added to allow the pH to reach 9. Thereafter, while adding dropwise the potassium hydroxide/ethanol solution so as to maintain the pH at 9 or higher, a 45% aqueous solution of hydrogen peroxide (5.39 g, 71.3 mmol, manufactured by Nippon Peroxide Co., Ltd.) was added dropwise in 30 minutes (the acetonitrile concentration in the system at this stage: 1.36 mol/L, pH=9.3). While maintaining the reaction temperature at 30° C. or lower, the potassium hydroxide/ethanol solution was added dropwise to allow the pH to reach 10.5 in two hours after the end of the dropwise addition of the aqueous hydrogen peroxide solution, and furthermore by stirring for two hours (stirring speed: 1500 rpm) while controlling the pH at 10.5, the reaction was completed (the acetonitrile concentration in the system at the end of the reaction: 0.72 mol/L). The reaction was carried out while monitoring the acetonitrile concentration in the system as needed. The reaction mixture was neutralized by adding a 15% by weight of $H_2SO_4$ aqueous solution and diluted by adding pure water (10 g), and the solvent was evaporated under reduced pressure. The residue was extracted with ethyl acetate (10 g). As shown in Table 1 below, by measuring the resulting solution by gas chromatography, it was determined that the conversion rate of the substrate, i.e., bisphenol A type diallylether, was 95.0%, the yield of a diepoxy monomer, i.e., bisphenol A type diglycidylether, was 49.9%, and that of a monoglycidylether was 38.6%. Since hydrogen peroxide self-decomposes under a basic condition, the residual concentration thereof in the system was measured in order to determine the rate consumed by the epoxidation reaction. As a result, the epoxidation selectivity of hydrogen peroxide was determined to be 46.3%. The epoxidation selectivity herein represents the percentage of the double bonds of the allylether groups in the substrate that are subjected to epoxidation, based on the amount consumed of hydrogen peroxide. In measurement of the acetonitrile concentration in the reaction mixture, acetonitrile in the mixture was determined (mol) by gas chromatography, and then the weight of each component charged was converted by using its specific gravity to obtain the volume (L). Based on these values, the acetonitrile concentration (mol/L) at each stage was calculated.

In addition, the conversion rate, yield and epoxidation selectivity of hydrogen peroxide were also determined based on the analysis results by gas chromatography as follows:

Conversion rate(%)=(1−moles of the residual substrate/moles of the substrate used)×100

Yield(%)=(moles of the objective compound/moles of the substrate used)×100

The yield was determined by calculating the weight of the objective compound based on a calibration curve and converting it to moles.

The epoxidation selectivity of hydrogen peroxide(%)= [{(moles of diglycidyl×2)+moles of monoglycidyl}/moles of the hydrogen peroxide consumed]×100

The residual concentration of hydrogen peroxide was determined by using as a measuring instrument a hydrogen peroxide counter HP-300 (manufactured by Hiranuma Sangyo Corporation) based on the principle of iodine coulometric titration (back-titration).

Examples 2-5 and Comparative Examples 1-3

A procedure similar to that of Example 1 was carried out; however, the amounts used of acetonitrile, hydrogen peroxide and ethanol relative to bisphenol A type diallylether were changed as shown in Table 1 below. The results are shown in Table 1 together with the result of Example 1. As shown in Comparative Example 1, when the amount of acetonitrile in the system during the reaction decreases to lower than 0.6 mol/L, the yield of the end objective product, i.e., a diepoxide, decreases. On the other hand, as shown in Comparative Examples 2 and 3, even if the amount used of acetonitrile in the system during the reaction is greater than 5 mol/L, the yield of a diepoxide does not significantly increase, while the epoxidation selectivity of hydrogen peroxide decreases.

TABLE 1

| | Molar ratio | | | | | | Temp. (° C.) | Acetonitrile mol/L | | | Conv. rate | Yield | | Epoxidation selectivity |
| | | | | | | | | At the initial stage of | After dropwise | At the end of | | | | |
| | Diallyl-ether | Aceto-nitrile | Hydrogen peroxide | Etha-nol | pH | Base | | the reaction | addition of $H_2O_2$ | the reaction | Diallyl-ether | Mono-epoxide | Di-epoxide | Hydrogen peroxide |
|---|---|---|---|---|---|---|---|---|---|---|---|---|---|---|
| Ex. 1 | 1.0 | 4.0 | 4.4 | 35.9 | 10.5 | KOH/EtOH | 30 | 1.56 | 1.36 | 0.72 | 95.0% | 38.6% | 49.9% | 46.3% |
| Ex. 2 | 1.0 | 4.0 | 4.4 | 55.7 | 10.5 | KOH/EtOH | 30 | 1.06 | 0.98 | 0.63 | 89.7% | 45.6% | 37.6% | 48.6% |
| Ex. 3 | 1.0 | 3.0 | 3.3 | 30.0 | 10.5 | KOH/EtOH | 30 | 1.37 | 1.22 | 0.78 | 84.8% | 44.1% | 34.2% | 62.1% |
| Ex. 4 | 1.0 | 3.0 | 4.4 | 33.3 | 10.5 | KOH/EtOH | 30 | 1.25 | 1.11 | 0.60 | 90.2% | 43.4% | 41.1% | 43.1% |
| Ex. 5 | 1.0 | 5.0 | 4.4 | 37.2 | 10.5 | KOH/EtOH | 30 | 1.83 | 1.65 | 1.19 | 93.8% | 40.9% | 49.8% | 50.1% |
| Comp. Ex. 1 | 1.0 | 2.0 | 4.4 | 32.4 | 10.5 | KOH/EtOH | 30 | 0.89 | 0.76 | 0.21 | 81.3% | 50.8% | 21.3% | 31.2% |
| Comp. Ex. 2 | 1.0 | 20.0 | 4.4 | 17.5 | 10.5 | KOH/EtOH | 30 | 8.44 | 7.51 | 6.18 | 95.2% | 36.5% | 50.6% | 35.0% |
| Comp. Ex. 3 | 1.0 | 20.0 | 4.4 | 8.0 | 10.5 | KOH/EtOH | 30 | 11.01 | 9.47 | 7.68 | 92.2% | 41.8% | 44.5% | 30.4% |

Example 6

Into a 50 mL separable flask of a reaction calorimeter (MultiMax, manufactured by Mettler Toledo), bisphenol A type diallylether (5.01 g, 16.2 mmol, manufactured by Qin yang Tianyi Chemical Co., Ltd.), acetonitrile (2.01 g, 49.0 mmol, manufactured by Junsei Chemical Co., Ltd.) and ethanol (22.44 g, 487.1 mmol, manufactured by Junsei Chemical Co., Ltd.) were charged. At this stage, the acetonitrile concentration in the system was 1.37 mmol/L and the pH was 8.2. Then, while maintaining the reaction temperature at 30° C., a potassium hydroxide (manufactured by Wako Pure Chemical Industries, Ltd.)/ethanol solution (KOH/EtOH=250 mg/mL) was added to allow the pH to reach 10.5. Thereafter, while adding dropwise the potassium hydroxide/ethanol solution as needed in order to control the pH at 10.5 until the end of the reaction, a 45% aqueous solution of hydrogen peroxide (4.04 g, 53.5 mmol, manufactured by Nippon Peroxide Co., Ltd.) was added dropwise in 30 minutes (the acetonitrile concentration in the system at this stage: 1.19 mol/L), and then by stirring for four hours (stirring speed: 1500 rpm), the reaction was completed (the acetonitrile concentration in the system at the end of the reaction: 0.67 mol/L). The reaction was carried out while monitoring the acetonitrile concentration in the system as needed. The reaction mixture was neutralized by adding a 15% by weight of $H_2SO_4$ aqueous solution and diluted by adding pure water (10 g), and the solvent was evaporated under reduced pressure. The residue was extracted with ethyl acetate (10 g). In measuring the resulting solution by gas chromatography, it was determined as shown in Table 2 that the conversion rate of the substrate, i.e., bisphenol A type diallylether, was 85.6%, the yield of a diepoxy monomer, i.e., bisphenol A type diglycidylether, was 33.9%, and that of a monoglycidylether was 45.5%. Based on the analysis of hydrogen peroxide, the epoxidation selectivity of hydrogen peroxide was determined to be 41.1%.

Examples 7-17 and Comparative Example 4

A procedure similar to that of Example 6 was carried out; however, the amounts used of acetonitrile, hydrogen peroxide and ethanol relative to bisphenol A type diallylether, and the pH, base and temperature were changed as shown in Table 2 below. Potassium carbonate used in Examples 8 and 14 and sodium hydroxide in Example 13 were manufactured by Junsei Chemical Co., Ltd., cesium hydroxide used in Example 15 was manufactured by Alfa Aesar, A Johnson Matthey Company, and tetramethyl ammonium hydroxide (TMAH) used in Examples 16 and 17 was manufactured by Sigma-Aldrich Japan K.K. The results are shown in Table 2 below together with the result of Example 6. As shown in Comparative Example 4, it is believed that the pH higher than 11 may cause low yield and low epoxidation selectivity of hydrogen peroxide. In Example 8, the conversion rate and yield were lower than those in other Examples. This would be because the side reaction was suppressed (the epoxidation selectivity (hydrogen peroxide) was high) due to a mild reaction condition in which the pH is 9, whereas the reaction rate decreased. Therefore, a longer reaction time would increase the conversion rate and yield.

TABLE 2

| Examples | Molar ratio | | | | pH | Base | Temp. (° C.) | Acetonitrile mol/L | | | Conv. rate | Yield | | Epoxidation selectivity |
| | Diallylether | Acetonitrile | Hydrogen peroxide | Ethanol | | | | At the initial stage of the reaction | After dropwise addition of $H_2O_2$ | At the end of the reaction | Diallylether | Monoepoxide | Diepoxide | Hydrogen peroxide |
| --- | --- | --- | --- | --- | --- | --- | --- | --- | --- | --- | --- | --- | --- | --- |
| Ex. 6 | 1.0 | 3.0 | 3.3 | 30.0 | 10.5 | KOH/EtOH | 30 | 1.37 | 1.19 | 0.67 | 85.6% | 45.5% | 33.9% | 41.1% |
| Ex. 7 | 1.0 | 4.0 | 2.2 | 28.1 | 10.5 | KOH/MeOH | 30 | 1.86 | 1.68 | 1.23 | 84.5% | 41.0% | 33.5% | 67.2% |
| Ex. 8 | 1.0 | 4.0 | 2.2 | 28.2 | 9.0 | $K_2CO_3$/MeOH | 30 | 1.77 | 1.63 | 1.57 | 11.2% | 6.8% | 3.1% | 73.3% |
| Ex. 9 | 1.0 | 4.0 | 2.2 | 28.2 | 10.0 | KOH/MeOH | 30 | 1.86 | 1.72 | 1.50 | 57.8% | 37.8% | 14.4% | 53.1% |
| Ex. 10 | 1.0 | 4.0 | 2.2 | 28.2 | 10.0 | KOH/MeOH | 50 | 1.87 | 1.64 | 1.14 | 72.1% | 41.1% | 16.8% | 37.2% |
| Ex. 11 | 1.0 | 4.0 | 2.2 | 28.3 | 11.0 | KOH/MeOH | 30 | 1.77 | 1.53 | 1.11 | 82.4% | 42.4% | 30.6% | 54.4% |
| Ex. 12 | 1.0 | 4.0 | 2.2 | 28.3 | 11.0 | KOH/MeOH | 40 | 1.76 | 1.50 | 1.06 | 78.1% | 47.6% | 26.7% | 45.5% |
| Ex. 13 | 1.0 | 4.0 | 2.2 | 28.2 | 11.0 | NaOH/MeOH | 30 | 1.75 | 1.64 | 1.10 | 80.0% | 46.3% | 26.9% | 55.8% |
| Ex. 14 | 1.0 | 4.0 | 2.2 | 28.1 | 11.0 | $K_2CO_3$/MeOH | 30 | 1.76 | 1.61 | 0.99 | 77.1% | 46.9% | 24.9% | 56.0% |
| Ex. 15 | 1.0 | 4.0 | 2.2 | 28.1 | 11.0 | CsOH/MeOH | 30 | 1.87 | 1.66 | 1.33 | 79.3% | 52.9% | 18.9% | 48.4% |
| Ex. 16 | 1.0 | 4.0 | 2.2 | 28.1 | 11.0 | TMAH/MeOH | 30 | 1.87 | 1.66 | 1.27 | 75.7% | 55.2% | 12.6% | 39.2% |
| Ex. 17 | 1.0 | 4.0 | 2.2 | 28.1 | 11.0 | TMAH aq. | 30 | 1.87 | 1.66 | 1.28 | 70.4% | 48.8% | 15.1% | 36.6% |
| Comp. Ex. 4 | 1.0 | 4.0 | 2.2 | 28.2 | 11.5 | KOH/MeOH | 30 | 1.56 | 1.16 | 0.51 | 50.5% | 25.7% | 2.6% | 7.0% |

Examples 18-20 and Comparative Example 5

In Examples 18-20, the reaction was carried out in a similar manner to Example 1; however, the solvent and base condition in Example 1 were changed to those described in Table 3 below and the amount of the solvent was 67% by weight. Propanol and butanol used in Examples 19 and 20 were 1-propanol and 1-butanol, both manufactured by Junsei Chemical Co., Ltd. In Comparative Example 5, a similar procedure was carried out by using acetonitrile as the solvent, instead of alcohol. These results are shown in Table 3 together with the result of Example 1 in which ethanol was used as the solvent. In Comparative Example 5 in which alcohol was not used as the solvent, the yield of a diepoxide was low. In Example 20 in which butanol was used, the yield of a diepoxide was low. This would be because the solubility of the substrate, i.e., bisphenol A type diallylether, in the butanol layer decreased by the dropwise addition of a 45% aqueous hydrogen peroxide solution and a potassium hydroxide/butanol solution.

324.2 mmol), which was weighted out to a 50 mL dropping funnel, was added dropwise in two hours (replenishment) (the acetonitrile concentration in the system at this stage: 0.91 mol/L). A 45% aqueous solution of hydrogen peroxide (53.92 g, 713.5 mmol) was simultaneously added dropwise in four hours (replenishment) by using a 100 mL dropping funnel, and then the reaction mixture was further stirred for four hours while controlling the pH at 10.5 to complete the reaction (the acetonitrile concentration at the end of the reaction: 0.62 mol/L). The reaction was carried out while monitoring the acetonitrile concentration in the system as needed. The reaction mixture was diluted by adding pure water (100 g), and the solvent was evaporated under reduced pressure. After the residue was extracted with ethyl acetate (100 g), pure water (100 g) was added again to separate the liquid. As shown in Table 4, by measuring the resulting solution by gas chromatography, it was determined that the conversion rate of the substrate, i.e., bisphenol A type diallylether, was 100%, the yield of a diepoxy monomer, i.e., bisphenol A type diglycidylether, was 87.7%, and that of monoglycidylether was 5.1%. Based on the analysis of hydrogen peroxide, the epoxidation selectivity of hydrogen peroxide was determined to be 23.9%.

TABLE 3

| | Molar ratio | | | | | | | Acetonitrile mol/L | | | | Yield | | Epoxidation |
| | | | | | | | | At the initial stage of the reaction | After dropwise addition of $H_2O_2$ | At the end of the reaction | Conv. rate Diallyl-ether | | | selectivity |
| | Di-allyl-ether | Aceto-nitrile | Hydrogen peroxide | Solvent (Molar Ratio) | pH | Base | Temp. (°C.) | | | | | Mono-epox-ide | Di-epox-ide | Hydrogen peroxide |
| --- | --- | --- | --- | --- | --- | --- | --- | --- | --- | --- | --- | --- | --- | --- |
| Ex. 1 | 1.0 | 4.0 | 4.4 | EtOH (35.9) | 10.5 | KOH/EtOH | 30 | 1.56 | 1.36 | 0.72 | 95.0% | 38.6% | 49.9% | 46.3% |
| Ex. 18 | 1.0 | 4.0 | 4.4 | MeOH (26.4) | 10.5 | KOH/MeOH | 30 | 1.56 | 1.36 | 0.65 | 83.8% | 41.7% | 34.9% | 31.9% |
| Ex. 19 | 1.0 | 4.0 | 4.4 | n-PrOH (28.1) | 10.5 | KOH/PrOH | 30 | 1.58 | 1.42 | 0.87 | 88.1% | 48.1% | 31.2% | 41.0% |
| Ex. 20 | 1.0 | 4.0 | 4.4 | n-BuOH (22.0) | 10.5 | KOH/BuOH | 30 | 1.59 | 1.43 | 0.84 | 54.4% | 44.6% | 4.0% | 12.0% |
| Comp. Ex. 5 | 1.0 | 31.7 | 4.4 | — | 10.5 | KOH/MeOH | 30 | 16.13 | 14.03 | 13.00 | 62.5% | 49.5% | 7.8% | 24.3% |

Example 21

Into a 1 L four-necked recovery flask, bisphenol A type diallylether (50.05 g, 162.3 mmol, manufactured by Qin yang Tianyi Chemical Co., Ltd.), acetonitrile (26.63 g, 648.7 mmol, manufactured by Junsei Chemical Co., Ltd.) and ethanol (265.1 g, 5754.2 mmol, manufactured by Junsei Chemical Co., Ltd.) were weighed out (at this stage, the acetonitrile concentration in the system was 1.55 mmol/L and the pH was 8.2). Then, after allowing the pH to reach 9 by adding an aqueous saturated potassium hydroxide solution (KOH/$H_2O$=110 mg/100 mL) prepared by using potassium hydroxide manufactured by Wako Pure Chemical Industries, Ltd., a 45% aqueous solution of hydrogen peroxide (53.92 g, 713.5 mmol, manufactured by Nippon Peroxide Co., Ltd.) was added dropwise in two hours by using a 100 mL dropping funnel (the acetonitrile concentration in the system at this stage: 1.18 mol/L, pH=9.2) while controlling the pH at 9 or higher by adding dropwise the aqueous saturated potassium hydroxide solution. While maintaining the reaction temperature at 30° C. or lower, an aqueous saturated potassium hydroxide solution was added dropwise to allow the pH to reach 10.5 in two hours after the end of the dropwise addition of the hydrogen peroxide aqueous solution, and the reaction mixture was further stirred for two hours while controlling the pH at 10.5 (the acetonitrile concentration in the system at this stage decreased to 0.61 mol/L). Then, acetonitrile (13.31 g,

Example 22

In this Example, the reaction was carried out in a similar manner to Example 1; however, the amounts charged in Example 1 were changed to bisphenol A type diallylether (3.02 g, 9.8 mmol, manufactured by Qin yang Tianyi Chemical Co., Ltd.), acetonitrile (2.41 g, 58.7 mmol, manufactured by Junsei Chemical Co., Ltd.), ethanol (24.13 g, 523.8 mmol, manufactured by Junsei Chemical Co., Ltd.) and a 45% aqueous solution of hydrogen peroxide (6.50 g, 86.0 mmol, manufactured by Nippon Peroxide Co., Ltd.). The variation in the acetonitrile concentration during the progress of the reaction was as follows: initial stage: 1.61 mol/L, after the dropwise addition of hydrogen peroxide: 1.36 mol/L, and at the end of the reaction: 0.60 mol/L. The results determined by gas chromatography indicate that the conversion rate of the substrate, i.e., bisphenol A type diallylether, was 99.8%, the yield of a diepoxy monomer, i.e., bisphenol A type diglycidylether, was 70.4%, and that of monoglycidylether was 19.2%. Based on the analysis of hydrogen peroxide, the epoxidation selectivity of hydrogen peroxide was determined to be 20.8%.

The results of Example 21 and Example 22 are shown together in Table 4 below.

TABLE 4

| | Molar ratio | | | | | | Acetonitrile mol/L | |
| | Diallyl-ether | Aceto-nitrile | Hydrogen peroxide | Ethanol | pH | Base | Temp. (° C.) | At the initial stage | Dropwise addition of H$_2$O$_2$ |
|---|---|---|---|---|---|---|---|---|---|
| Ex. 21 | 1.0 | 4 + 2 [Replenished] | 4.4 + 4.4 [Replenished] | 53.5 | 10.5 | KOH aq. | 30 | 1.55 | 1.18 |
| Ex. 22 | 1.0 | 6.0 | 8.8 | 53.5 | 10.5 | KOH/EtOH | 30 | 1.61 | 1.36 |

| | Acetonitrile mol/L | | | Conv. rate | Yield | | Epoxidation selectivity |
| | Before addition | After addition | At the end of the reaction | Diallyl-ether | Mono-epoxide | Di-epoxide | Hydrogen peroxide |
|---|---|---|---|---|---|---|---|
| Ex. 21 | 0.61 | 0.91 | 0.62 | 100.0% | 5.1% | 87.7% | 23.9% |
| Ex. 22 | — | — | 0.60 | 99.8% | 19.2% | 70.4% | 20.8% |

Even though the reaction scales are different between Examples 21 and 22, the overall ratios used of acetonitrile and hydrogen peroxide to bisphenol A type diallylether were the same. In Example 21, acetonitrile and hydrogen peroxide were added in two steps, whereas in Example 22 they were added at one step. By replenishing acetonitrile and hydrogen peroxide, the yield of the end objective product, i.e., a diepoxide, was improved, indicating the effectiveness of replenishment.

Example 23

To a 500 mL three-necked recovery flask equipped with a magnetic stirrer, cyclohexanedimethanol diallylether (100.0 g, 0.45 mol, manufactured by Asahi Kagaku Kogyo Co., Ltd.), acetonitrile (73.2 g, 1.78 mol, manufactured by Junsei Chemical Co., Ltd.) and methanol (92.9 g, 2.90 mol, manufactured by Junsei Chemical Co., Ltd.) were weighed out (the acetonitrile concentration in the system at this stage: 4.50 mol/L, pH=8.2). Using a water bath, the system was warmed to a temperature of 35° C., and the pH was allowed to reach 10.5 by adding an aqueous saturated potassium hydroxide solution (KOH/H$_2$O=110 mg/100 mL). While maintaining the reaction temperature at 40° C. or lower, until the end of the reaction, the aqueous saturated potassium hydroxide solution was added as needed in order to control the pH in the range of 10.75-10.25. After adding dropwise a 45% aqueous solution of hydrogen peroxide (101.1 g, 1.34 mol, manufactured by Nippon Peroxide Co., Ltd.) for 16 hours by using a 300 mL dropping funnel (the acetonitrile concentration in the system at this stage: 2.54 mol/L), the reaction mixture was further stirred for 10 hours to complete the reaction (the acetonitrile concentration at the end of the reaction: 2.14 mol/L). The reaction was carried out while monitoring the acetonitrile concentration in the system as needed. In measuring the reaction mixture by gas chromatography, it was determined that the conversion rate of the substrate, i.e., cyclohexanedimethanol diallylether, was 100%, the yield of a diepoxy, i.e., cyclohexanedimethanol diglycidylether, was 88.5%, and that of monoglycidylether was 2.6%. Based on the analysis of hydrogen peroxide, the epoxidation selectivity of hydrogen peroxide was determined to be 73.8%.

Example 24

To a 300 mL three-necked recovery flask equipped with a magnetic stirrer, cyclohexanedimethanol diallylether (50.0 g, 0.22 mol, manufactured by Asahi Kagaku Kogyo Co., Ltd.), a crude acetonitrile (33.7 g, 0.67 mol) with a purity of 82% obtained as a byproduct of acrylonitrile production by the Sohio process and methanol (46.4 g, 2.90 mol, manufactured by Junsei Chemical Co., Ltd.) were weighed out (the acetonitrile concentration in the system at this stage: 3.44 mol/L, pH=6.3). Using a water bath, the system was warmed to a temperature of 35° C., and the pH was allowed to reach 10.5 with a potassium hydroxide/methanol solution (KOH/MeOH=250 mg/mL). While maintaining the reaction temperature at 40° C. or lower, until the end of the reaction, the potassium hydroxide/methanol solution was added as needed in order to control the pH in the range of 10.75-10.25. After adding dropwise a 45% aqueous solution of hydrogen peroxide (50.5 g, 0.67 mol, manufactured by Nippon Peroxide Co., Ltd.) for 16 hours by using a 100 mL dropping funnel (the acetonitrile concentration in the system at this stage: 1.20 mol/L), the reaction mixture was further stirred for 14 hours to complete the reaction (the acetonitrile concentration at the end of the reaction: 0.88 mol/L). The reaction was carried out while monitoring the acetonitrile concentration in the system as needed. In measuring the reaction mixture by gas chromatography, it was determined that the conversion rate of the substrate, i.e., cyclohexanedimethanol diallylether, was 99.9%, the yield of a diepoxy, i.e., cyclohexanedimethanol diglycidylether was 79.8%, and that of monoglycidylether was 2.9%. Based on the analysis of hydrogen peroxide, the epoxidation selectivity of hydrogen peroxide was determined to be 65.4%.

Since cyclohexanedimethanol diallylether is more soluble in an alcohol solvent than bisphenol A type diallylether, the amount required of alcohol can be reduced. Thus, in the reactions of Examples 23 and 24 in which cyclohexanedimethanol diallylether was used as the substrate, as compared to the reactions in Examples 1-22 in which bisphenol A type diallylether was used as the substrate, the upper limit of the acetonitrile concentration suitable for the reaction may be higher.

INDUSTRIAL APPLICABILITY

The method for producing an epoxy compound according to the present invention can safely produce the epoxy compound by reacting an organic compound having a carbon-carbon double bond and hydrogen peroxide in a simple procedure with high efficiency and low cost, and thus is industrially useful.

The invention claimed is:

1. A method of producing an epoxy compound comprising epoxidizing the carbon-carbon double bond of an organic compound having a carbon-carbon double bond in the presence of acetonitrile by using hydrogen peroxide as an oxidizing agent, wherein the reaction proceeds while controlling the acetonitrile concentration in the reaction system in the range of 0.6-2 mol/L by using a solvent containing an alcohol, wherein the organic compound having a carbon-carbon double bond is bisphenol A type diallylether and/or bisphenol F type diallylether.

2. The method of producing an epoxy compound according to claim 1, wherein the ratio of the total amount used of acetonitrile to the total amount used of hydrogen peroxide (acetonitrile/hydrogen peroxide (molar ratio)) in the reaction is in the range of 0.6-2.

3. The method of producing an epoxy compound according to claim 1, wherein the ratio of the total amount used of acetonitrile to the total amount used of the organic compound having a carbon-carbon double bond (acetonitrile/the carbon-carbon double bond of the organic compound having a carbon-carbon double bond (molar ratio)) in the reaction is in the range of 1.2-5.

4. The method of producing an epoxy compound according to claim 1, wherein the pH of the reaction mixture during the progress of the reaction is in the range of 9-11.

5. The method of producing an epoxy compound according to claim 1, wherein the alcohol is at least one selected from C1-C4 alcohols.

6. The method of producing an epoxy compound according to claim 1, wherein the temperature of the reaction mixture is controlled in the range of 20-100° C.

7. The method of producing an epoxy compound according to claim 1, wherein acetonitrile is added to a concentration of 2 mol/L or less before the acetonitrile concentration in the reaction system reaches less than 0.6 mol/L as the reaction proceeds.

8. The method of producing an epoxy compound according to claim 1, wherein the acetonitrile is a crude acetonitrile obtained as a byproduct of acrylonitrile production by the Sohio process.

9. The method of producing an epoxy compound according to claim 2, wherein the ratio of the total amount used of acetonitrile to the total amount used of the organic compound having a carbon-carbon double bond (acetonitrile/the carbon-carbon double bond of the organic compound having a carbon-carbon double bond (molar ratio)) in the reaction is in the range of 1.2-5.

10. The method of producing an epoxy compound according to claim 4, wherein the method further comprises controlling the pH of the reaction mixture in the range of 10-11.

11. The method of producing an epoxy compound according to claim 10, wherein the pH of the reaction mixture at the initial stage of the reaction is adjusted in the range of 9-10.

12. A method of producing an epoxy compound comprising epoxidizing the carbon-carbon double bond of an organic compound having a carbon-carbon double bond in the presence of acetonitrile by using hydrogen peroxide as an oxidizing agent, wherein the reaction proceeds while controlling the acetonitrile concentration in the reaction system in the range of 0.6-5 mol/L by using a solvent containing an alcohol, and the organic compound having a carbon-carbon double bond is an alicyclic polyallylether, wherein the alicylic polyallylether is at least one selected from the group consisting of 1,4-cyclohexanedimethanol diallylether and tricyclo[$5.2.1.0^{2.6}$] decanedimethanol diallylether.

* * * * *